(12) United States Patent
Tanaka et al.

(10) Patent No.: US 7,183,435 B2
(45) Date of Patent: Feb. 27, 2007

(54) TRIPHENYLENE COMPOUND, METHOD FOR MAKING

(75) Inventors: Yuuji Tanaka, Fujinomiya (JP); Tomoyuki Shimada, Shizuoka-ken (JP)

(73) Assignee: Ricoh Company, Ltd., Tokyo (JP)

( * ) Notice: Subject to any disclaimer, the term of this patent is extended or adjusted under 35 U.S.C. 154(b) by 13 days.

(21) Appl. No.: 11/190,856

(22) Filed: Jul. 28, 2005

(65) Prior Publication Data

US 2006/0024595 A1 Feb. 2, 2006

(30) Foreign Application Priority Data

Jul. 28, 2004 (JP) ............................. 2004-220693

(51) Int. Cl.
*C07C 211/00* (2006.01)
(52) U.S. Cl. .................................... 564/306
(58) Field of Classification Search ............... 564/305, 564/306, 307, 308, 321, 322
See application file for complete search history.

(56) References Cited

U.S. PATENT DOCUMENTS

| | | | |
|---|---|---|---|
| 4,886,846 A | 12/1989 | Shimada et al. |
| 4,916,039 A | 4/1990 | Hashimoto et al. |
| 4,931,350 A | 6/1990 | Shimada et al. |
| 5,047,590 A | 9/1991 | Shimada et al. |
| 5,059,708 A | 10/1991 | Aruga et al. |
| 5,068,350 A | 11/1991 | Hashimoto et al. |
| 5,081,233 A | 1/1992 | Sasaki et al. |
| 5,097,022 A | 3/1992 | Sasaki et al. |
| 5,098,807 A | 3/1992 | Shimada et al. |
| 5,166,438 A | 11/1992 | Hashimoto et al. |
| 5,219,692 A | 6/1993 | Shimada et al. |
| 5,233,090 A | 8/1993 | Shimada et al. |
| 5,248,826 A | 9/1993 | Sasaki et al. |
| 5,250,377 A | 10/1993 | Shimada et al. |
| 5,252,750 A | 10/1993 | Hashimoto et al. |
| 5,260,156 A | 11/1993 | Hashimoto et al. |
| 5,298,661 A | 3/1994 | Shimada et al. |
| 5,312,707 A | 5/1994 | Ota et al. |
| 5,319,069 A | 6/1994 | Sasaki et al. |
| 5,334,470 A | 8/1994 | Shimada et al. |
| 5,356,742 A | 10/1994 | Shimada et al. |
| 5,382,692 A | 1/1995 | Shimada et al. |
| 5,403,950 A | 4/1995 | Shimada et al. |
| 5,420,332 A | 5/1995 | Shimada et al. |
| 5,434,028 A | 7/1995 | Shimada et al. |
| 5,436,100 A | 7/1995 | Shimada et al. |
| 5,457,232 A | 10/1995 | Tanaka et al. |
| 5,459,275 A | 10/1995 | Tanaka et al. |
| 5,462,826 A | 10/1995 | Shimada et al. |
| 5,475,137 A | 12/1995 | Shimada et al. |
| 5,480,753 A | 1/1996 | Shimada et al. |
| 5,488,164 A | 1/1996 | Shimada et al. |
| 5,489,495 A | 2/1996 | Anzai et al. |
| 5,547,792 A | 8/1996 | Shimada et al. |

(Continued)

FOREIGN PATENT DOCUMENTS

JP 2006039313 * 2/2006

*Primary Examiner*—Thurman K. Page
*Assistant Examiner*—Karl J. Puttlitz
(74) *Attorney, Agent, or Firm*—Oblon, Spivak, McClelland, Maier & Neustadt, P.C.

(57) ABSTRACT

The present invention relates to triphenylene compounds useful, for example, in an electrophotographic photoreceptor, and to a method for manufacturing these compounds.

5 Claims, 1 Drawing Sheet

U.S. PATENT DOCUMENTS

| | | | |
|---|---|---|---|
| 5,550,293 A | 8/1996 | Shimada et al. |
| 5,569,800 A | 10/1996 | Aruga et al. |
| 5,576,132 A | 11/1996 | Tanaka et al. |
| 5,599,995 A | 2/1997 | Tanaka et al. |
| 5,616,801 A | 4/1997 | Shimada et al. |
| 5,616,805 A | 4/1997 | Tanaka et al. |
| 5,623,062 A | 4/1997 | Sasaki et al. |
| 5,631,404 A | 5/1997 | Anzai et al. |
| 5,641,598 A | 6/1997 | Tanaka et al. |
| 5,663,407 A | 9/1997 | Shimada et al. |
| 5,672,728 A | 9/1997 | Tanaka et al. |
| 5,672,756 A | 9/1997 | Shimada et al. |
| 5,723,243 A | 3/1998 | Sasaki et al. |
| 5,747,204 A | 5/1998 | Anzai et al. |
| 5,789,128 A | 8/1998 | Adachi et al. |
| 5,808,155 A | 9/1998 | Shimada et al. |
| 5,830,980 A | 11/1998 | Anzai et al. |
| 5,840,454 A | 11/1998 | Nagai et al. |
| 5,846,680 A | 12/1998 | Adachi et al. |
| 5,853,935 A | 12/1998 | Suzuki et al. |
| 5,910,561 A | 6/1999 | Adachi et al. |
| 5,942,363 A | 8/1999 | Tanaka et al. |
| 5,981,124 A | 11/1999 | Shimada et al. |
| 6,018,014 A | 1/2000 | Nagai et al. |
| 6,027,846 A | 2/2000 | Shimada et al. |
| 6,066,757 A | 5/2000 | Tanaka et al. |
| 6,069,224 A | 5/2000 | Adachi et al. |
| 6,093,784 A | 7/2000 | Tamura et al. |
| 6,103,435 A | 8/2000 | Shimada et al. |
| 6,132,914 A | 10/2000 | Shimada |
| 6,184,362 B1 | 2/2001 | Shimada et al. |
| 6,191,249 B1 | 2/2001 | Tanaka et al. |
| 6,271,356 B1 | 8/2001 | Shimada et al. |
| 6,316,577 B1 | 11/2001 | Shimada et al. |
| 6,333,439 B1 | 12/2001 | Shimada |
| 6,448,384 B1 | 9/2002 | Shimada |
| 6,465,648 B1 | 10/2002 | Tadokoro et al. |
| 6,492,079 B2 | 12/2002 | Shimada et al. |
| 6,544,701 B2 | 4/2003 | Tadokoro et al. |
| 6,548,216 B2 | 4/2003 | Kawamura et al. |
| 6,596,449 B2 | 7/2003 | Shimada et al. |
| 6,861,188 B2 | 3/2005 | Ikegami et al. |
| 2003/0198881 A1 | 10/2003 | Kawamura et al. |
| 2004/0126687 A1 | 7/2004 | Ikegami et al. |
| 2004/0131960 A1 | 7/2004 | Kawamura et al. |
| 2004/0170911 A1 | 9/2004 | Shimada et al. |
| 2004/0180280 A1 | 9/2004 | Ikegami et al. |
| 2005/0008957 A1 | 1/2005 | Ikegami et al. |

* cited by examiner

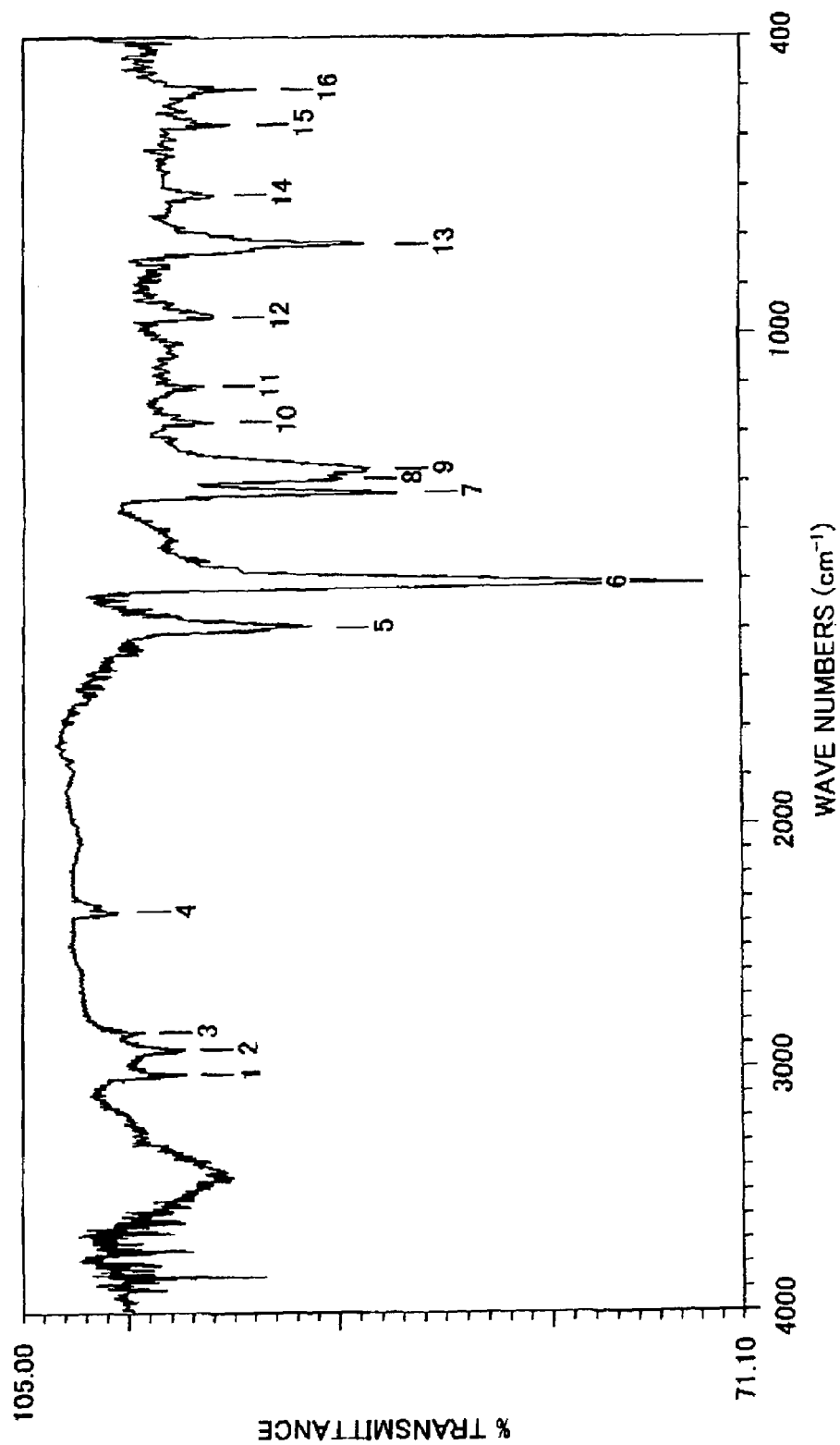
FIGURE

TRIPHENYLENE COMPOUND, METHOD FOR MAKING

REFERENCE TO EARLIER APPLICATIONS

This application claims priority to Japanese application 2004-220693 filed Jul. 28, 2004, incorporated herein by reference.

BACKGROUND OF THE INVENTION

1. Field of the Invention

The present invention relates to triphenylene compounds useful, for example, in an electrophotographic photoreceptor, and to a method for manufacturing these compounds.

2. Discussion of the Background

Recently, information-processing systems using electrophotographic methods are making a remarkable progress. In particular, laser printers and digital copiers which record data with light by changing the data into digital signals make remarkable improvements in their printing qualities and reliabilities. Further, technologies used in these printers and copiers are applied to laser printers and digital copiers capable of printing full-color images with high-speed printing technologies. Because of these reasons, photoreceptors are required both to produce high-quality images and to have high durability.

Photoreceptors using organic photosensitive materials are widely used for these laser printers and digital copiers due to their cost, productivity and non-polluting properties. The organic photoreceptors are generally classified to a single-layered type and a functionally-separated type. The first practical organic photoreceptor, i.e., PVK-TNF charge transfer complex photoreceptor was the former single-layered type. In 1968, Mr. Hayashi and Mr. Regensburger independently invented PVK/a-Se multi-layered photoreceptor. In 1977, Mr. Melz, and in 1978, Mr. Schlosser disclosed a multi-layered photoreceptor whose photosensitive layers are all formed from organic materials, i.e., inorganic-pigment dispersed layer and an organic low-molecular-weight material dispersed polymer layer. These are called as functionally-separated photoreceptors because of having a charge generation layer (CGL). generating a charge by absorbing light and a charge transport layer (CTL), transporting the charge and neutralizing the charge on a surface of the photoreceptor. The multi-layered photoreceptor has much more improved sensitivity and durability than the single-layered photoreceptor. In addition, since materials can be separately selected for a charge generation material (CGM) and a charge transport material (CTM), a choice range of the materials is largely expanded. Because of these reasons, the multi-layered photoreceptor is now prevailing in the market.

A mechanism to form an electrostatic latent image in the multi-layered photoreceptor is as follows:
- the photoreceptor is charged and irradiated with light;
- the light passes through the CTL and is absorbed by the CGM in the CGL to generate a charge; the charge is injected into the CTL at an interface of the CGL and the CTL; and
- the charge moves in the CTL by an electric field and neutralizes the charge on the surface of the photoreceptor to form an electrostatic latent image.

Recently, in accordance with speeding up of the printing speed and downsizing of an image forming apparatus, the photoreceptor has to have a smaller diameter, so rapid response and stability thereof become a more important subject.

The following are commercially available charge transport materials that are conventionally known:

1,1-bis(p-diethylaminophenyl)-4,4-diphenyl-1,3-butadiene (Japanese Laid-Open Patent Application 62-30255), 5-[4-(N,N-di-p-tolylamino)amino)benzylidine]-5H-dibenzo[a,b]cycloheptene (Japanese Laid-Open Patent Application 63-225660), 9-methylcarbazole-3-aldehyde1,1-diphenyl, pyrene-1-aldehyde1,1-hydrazone, diphenylhydrazone (Japanese Laid-Open Patent Application 58-159536). 4'-bis(4-methylphenyl)amino-α-phenylstilbene, N,N'-diphenyl-N,N'-bis(3-methylphenyl)-[1,1'-biphenyl]-4,4'-diamine, and 9,9-dimethyl-2-(di-p-tolylamino)fluorene.

The charge transport layer is generally a film with a thickness of about 10 to 30 μm made from a solid solution in which a low-molecular weight charge transport material is dispersed in a binder resin. Most of the currently available photoconductors employ as a binder resin for the charge transport layer a bisphenol polycarbonate resin or a copolymer consisting of a monomer of the above-mentioned polycarbonate resin and any other monomers. However those charge transport material are not sufficient to satisfy rapid response to the process speed of the future.

On the contrary, molecular design about those charge transport material of rapid response(high mobility) are tabulated in the Society of Electrophotography of Japan, 25 (3), 16 (1986). In other words phenylamine group (>N-phenyl) as a functional group, the number of phenylamine group (>N-phenyl) are related to high mobility clearly.

Present compound which have multifunctional group bring rapid response to pass on this basis.

SUMMARY OF THE INVENTION

It is one object of this invention to provide compounds which have stability, rapid response and good transportability. Another object is to provide a method for manufacturing such compounds.

BRIEF DESCRIPTION OF THE DRAWINGS

The infrared absorption spectrum (KBr pellet method) of chemical compound (8) is shown in FIG. 1.

DETAILED DESCRIPTION OF THE PREFERRED EMBODIMENTS

These objects have been achieved by the discovery of triphenylene compounds of formula 1:

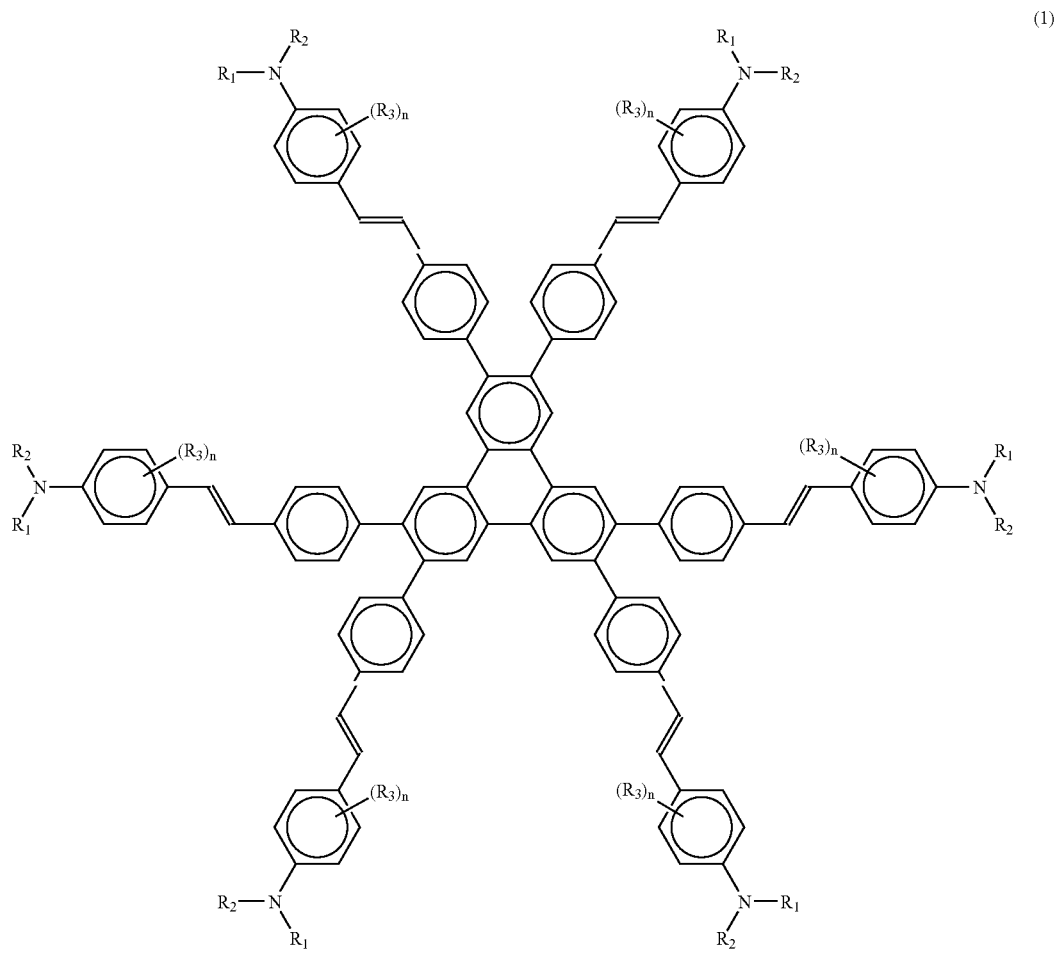

(1)

wherein:

R1 and R2 independently represent a substituted or unsubstituted alkyl group, or a substituted or unsubstituted aromatic hydrocarbon group and may be combined with each other to form a substituted or unsubstituted heterocyclic group including the nitrogen atom to which they are appended;

R3 independently represents a hydrogen atom, a substituted or unsubstituted alkyl group, a substituted or unsubstituted alkoxy group, a substituted or unsubstituted aromatic hydrocarbon group, or a halogen atom; and n independently represents an integer of from 1 to 4.

Specific examples of the alkyl group include methyl, ethyl, propyl, butyl, hexyl, undecanyl, etc. Preferably the alkyl group includes from 1–25 carbon atoms, more preferably 1–12.

Examples of the aromatic hydrocarbon group include benzene, biphenyl, naphthalene, anthracene, fluorine, pyrene, etc. Preferably the aromatic hydrocarbon group includes from 1–35 carbon atoms, more preferably 1–18.

Examples of the heterocycles include pyridine, quinoline, thiophen, furan, oxazole, oxadiazole, carbazole, etc.

Examples of the alkoxy group include methoxy, ethoxy, propoxy group, butoxy, etc. Halogen atom include fluorine, chlorine, bromine, iodine, etc.

Preferred groups include pyrrolidine, piperidine, and piperazine. Furthermore, when R1, R2 are connected each other, and a heterocyclic group including nitrogen atom is formed, the following are included in those structures that may be formed: a pyrrolidino radical, a piperidino radical, and a piperazino radical.

A preferred method for manufacturing the compounds of above formula (1) comprises reacting 2,3,6,7,10,11-hexabromotriphenylene having the following formula (2) with at least one boron compound having the following formula (3) and/or (4):

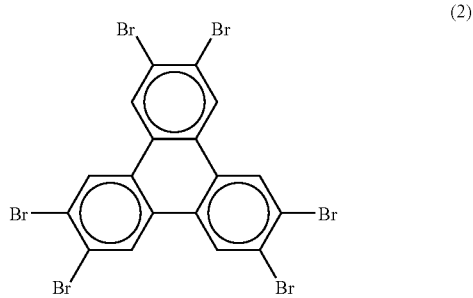

(2)

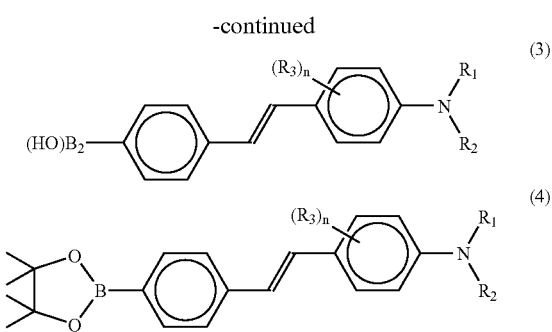

where in formula (3) and (4) R1, R2, and R3 are the same as in formula (1).

The invention triphenylene compounds are useful in organic photoconductors which have rapid response and high stability. The invention triphenylene compounds are new and can act as photoconducting materials as described above and are useful in, e.g., the photosensitive layer of a photoconductor for electrophotography as a charge transport substance. These compounds are especially useful in a detached type photosensitive layer having a charge transport layer and a charge generation material, and can provide a photoconductor which has high sensitivity, rapid response and stability.

Preferred processes of manufacturing the invention triphenylene compound include reacting 2,3,6,7,10,11-hexabromotriphenylene having formula (2) with at least one boron compound having formula (3) and/or (4), for example in the presence of palladium and optionally a base. Salts of compounds of formulae (3) and (4) or admixtures of salt(s) and non-salts maybe used. Reaction temperatures maybe, for example, about 100–250° C.

Useful solvents for reaction include:
water, alcohols such as methanol, ethanol and a propanol, mromatic hydrocarbons such as benzene, toluene and xylene, methylene chloride, chloroform,
haloalkanes such as dichloroethane,
halogenated aromatic hydrocarbons such as dichlorobenzene,
dioxane, tetrahydrofuran and ethers such as anisole,
esters such as ethyl acetate and butyl acetate,
ketones such as acetone and a methyl ethyl ketone,
nitrites such as acetonitrile,
amides such as N, a N-dimethylformamide and N,N-dimethyl acetamide,
sulfoxides such as dimethyl sulfoxide,
and mixtures thereof.

Specific examples of bases (alkali) useful herein include potassium acetate, potassium carbonate, NaHCO3, sodium carbonate, triethylamine, and mixtures thereof. The content of alkali is for example 1 to 3 times by mol that of the total of compounds of Formulae (3) and (4).

Specific examples of useful catalysts include inorganic palladium such as chlorinated palladium salts, organic palladium salts such as acetic acid palladium, organic palladium complexes such as Tetrakis(triphenylphosphine)Palladium (0) tetrakis(triphenylphosphine)palladium (0), bis (triphenylphosphine)palladium (II) dichloride, 1,1'-bis (diphenylphosphino)ferrocene palladium (II) dichloride. The quantity of the catalyst used can be, e.g, 0.001–0.5 times by mol that of the total of compounds of Formulae (3) and (4).

For exemplification of alkyl group in illustration of general formula: methyl group, ethyl group, propyl group, butyl group, hexyl group and undecanil group.

In addition, Specific Example of substituent, alkyl group such as C1–C12,

Alkoxy group such as methoxy group, ethoxy group, a propoxy group, a butoxy group, or fluorine atom, chlorine atom, bromine atom, halogen atom of iodine atom, Radix of heterocycle such as the aromatic hydrocarbon radical and pyrrolidine, piperidine, piperazine.

Furthermore, when R1, R2 couple each other, and heterocyclic group including nitrogen atom is formed, the fused heterocycle radical can be pyrrolidino, piperidino, piperazino, etc.

The new triphenylene compounds of formula (1) of the present invention are extremely useful as photoconductor materials in photoconductor for electrophotography.

Furthermore, these compounds are useful as charge transport materials assumed to be material where organic color or inorganic pigments generate charge for functionally separated electrophotographic photoreceptor.

2,3,6,7,10,11-hexabromotriphenylene may be obtained according to Tetrahedron.38.863(1982).

Compounds of the present invention can be combined with one or more pigments and/or dyes. Specific examples of useful organic-pigments include CI Pigment Blue 25 (color index CI 21180), CI Pigment Red 41 (CI 21200), CI Acid Red 52 (CI 45100), CI Basic Red 3 (CI 45210), an azo pigment having a carbazole skeleton disclosed in Japanese Laid-Open Patent Publication (JLPP) No. 53-95033, an azo pigment having a distyrylbenzene skeleton disclosed in JLPP No.53-133445, an azo pigment having a triphenylamine skeleton disclosed in JLPP No. 53-132347, an azo pigment having a dibenzothiophene skeleton disclosed in JLPP No. 54-21728, an azo pigment having an oxadiazole skeleton disclosed in JLPP No. 54-12742, an azo pigment having a fluorenone skeleton disclosed in JLPP No. 54-22834, an azo pigment having a bisstilbene skeleton disclosed in JLPP No. 54-17733, an azo pigment having a distyryloxadiazole skeleton disclosed in JLPP No. 54-2129, an azo pigment having a distyrylcarbazole skeleton disclosed in JLPP No. 54-14967 and an azo pigment having a benzanthrone skeleton; phthalocyanine pigments such as CI Pigment Blue 16 (CI 74100), Y-type oxotitaniumphthalocyanine disclosed in JLPP No. 64-17066, A(&bgr;)-type oxotitaniumphthalocyanine, B (&agr;)-type-type oxotitaniumphthalocyanine, I-type oxotitaniumphthalocyanine disclosed in JLPP No. 11-21466, II-type chlorogalliumphthalocyanine disclosed by Mr. Iijima and others in the 67th spring edition 1B4, 04 published by Chemical Society of Japan in 1994, V-type hydroxygalliumphthalocyanine disclosed Mr. Daimon and others in the 67th spring edition 1B4, 05 published by Chemical Society of Japan in 1994 and X-type metal-free phthalocyanine disclosed in U.S. Pat. No. 3,816,118; indigo pigments such as CI Vat Brown 5 (CI 73410) and CI Vat Dye (CI 73030); perylene pigments such as (Algo Scarlet B from Bayer Ltd and Indanthrene Scarlet R. from Bayer Ltd), and mixtures thereof.

Useful inorganic-pigment include Se, Se—Te, cadmium sulfide, α-Si etc. and mixtures thereof.

These materials (inorganic and organic) can be used alone or in combination.

EXAMPLES

Example 1

Preparation of 2,3,6,7,10,11-hexabromotriphenylene 2,3,6,7,10,11-hexabromotriphenylene may be prepared by reaction (5)

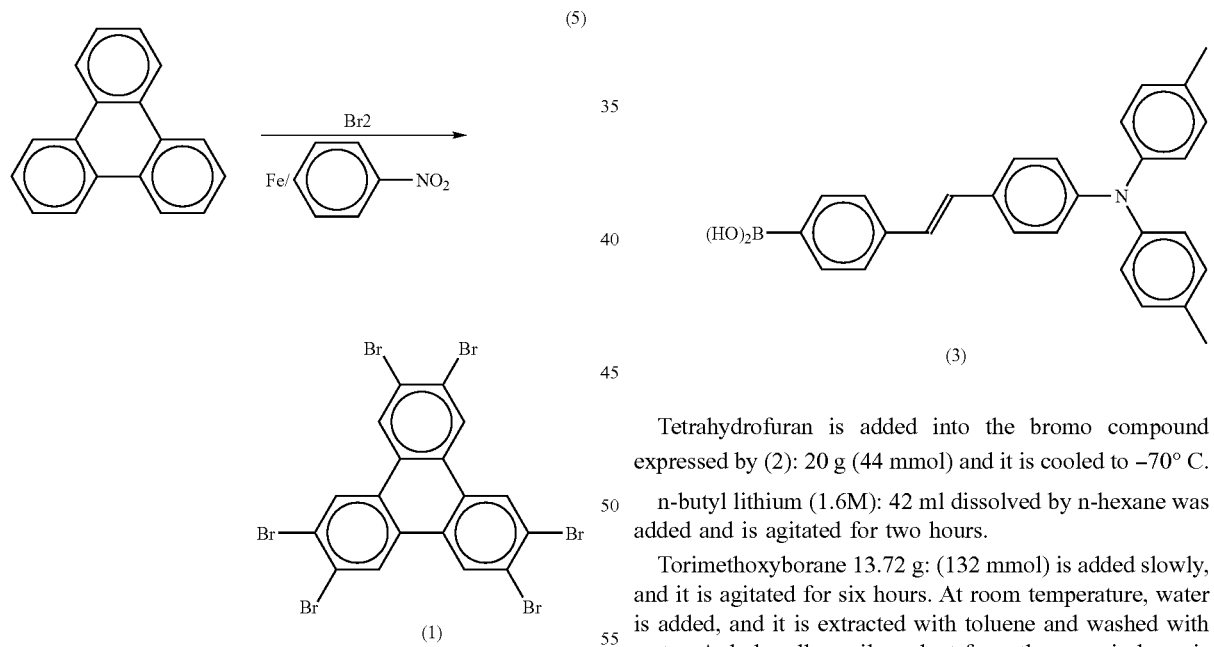

A mixture of 1.00 g (4.38 mmol) of triphenylene and 90 mg of Fe is dissolved in 20 ml of nitrobenzene and stirred for 3 hours at 205° C.

3.15 g (39.42 mmol) of bromine is added dropwise with stirring for 3 hours at room temperature and furthermore, for 3 hours at 205° C. When the mixture is cooled, 50 ml of ether is added and filtered. The solid which is precipitated is washed with ether and acetone and 3.00 g (yield: 97.6%) of hexabromo triphenylene is obtained.

Example 2

Preparation of a Boron Compound

A boron compound according to the invention may be prepared by reaction (6)

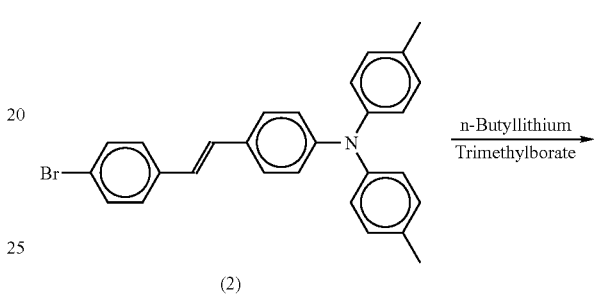

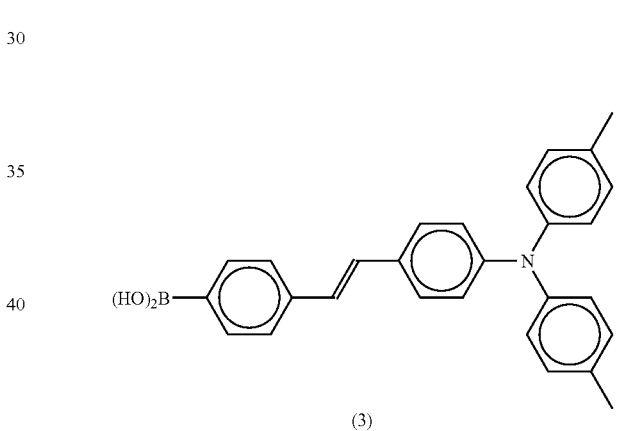

Tetrahydrofuran is added into the bromo compound expressed by (2): 20 g (44 mmol) and it is cooled to −70° C.

n-butyl lithium (1.6M): 42 ml dissolved by n-hexane was added and is agitated for two hours.

Torimethoxyborane 13.72 g: (132 mmol) is added slowly, and it is agitated for six hours. At room temperature, water is added, and it is extracted with toluene and washed with water. A dark yellow oil product from the organic layer is vacuum condensed and filtered by silica column chromatography {Eluant:toluene/dichloromethane (1/1) vol} to yield a yellow amorphous boron compound (3): 18.20 g (98.6%).

Example 3

Preparation of Triphenylene Compound

A triphenylene compound may be prepared by reaction (7):

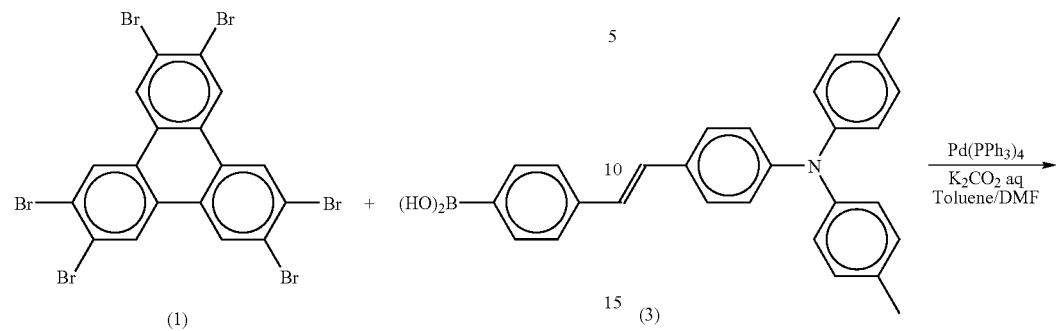
(7)
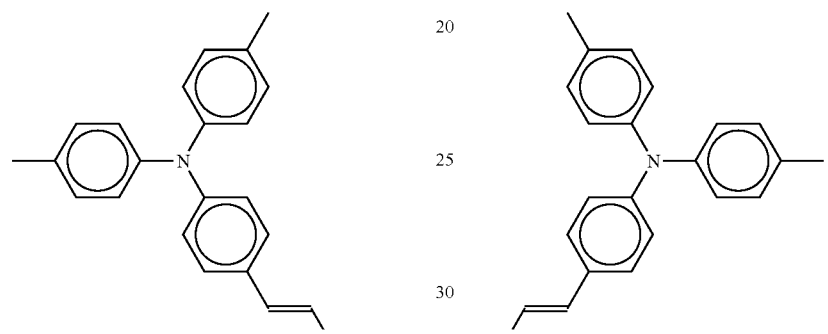
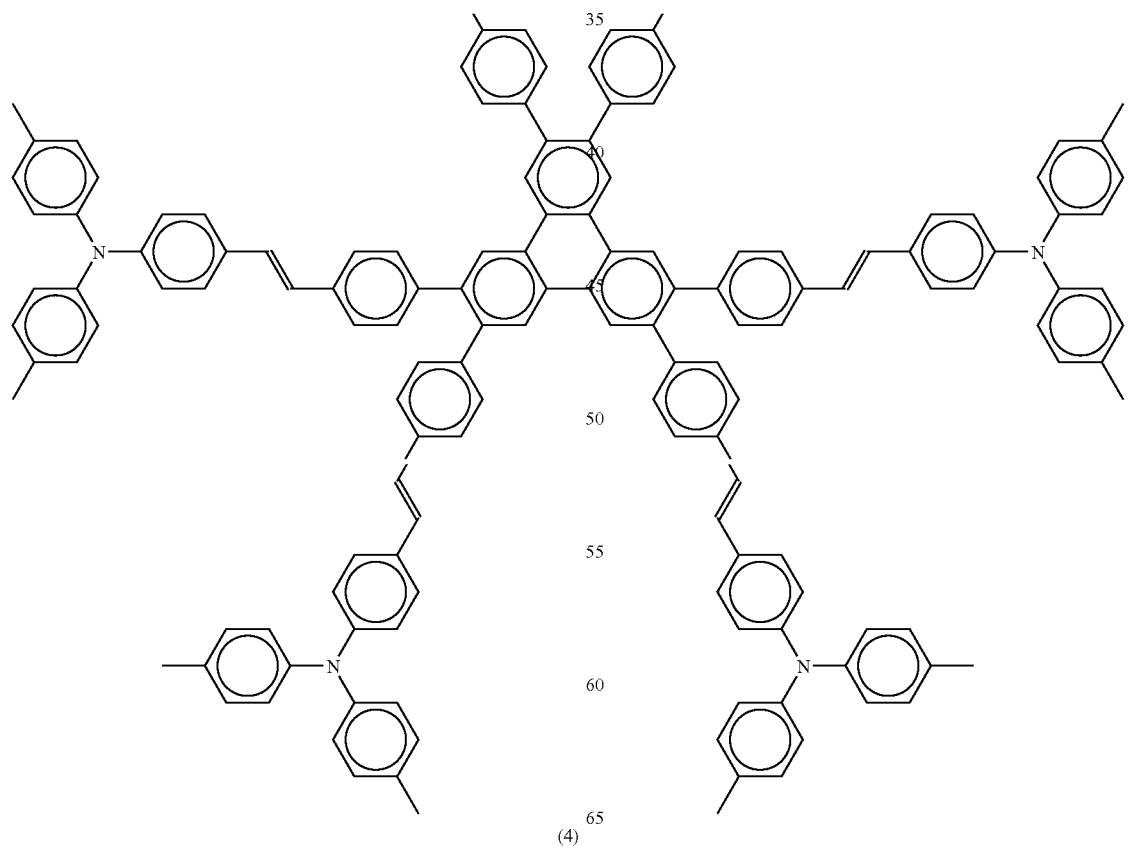
(4)

The mixture of hexabromo triphenylene (1): 0.3 g (0.427 mmol)
boron compound (3): 1.611 g (3.843 mmol), K2CO2: 0.796 g
Tetrakis(triphenylphosphine)palladium (0): 1.332 g (1.234 mmol), DMF: 10 ml, H2O: 5 ml, and o-dichlorobenzene: 40 ml is agitated for 7 hours at 125° C. and cooled off to room temperature and water is added. After that it is extracted with toluene and washed with water.

A dark yellow oil product from the organic layer is vacuum condensed and filtered by silica column chromatography [Eluant: MDC/n-hexan (1/2) vol] to provide a yellow amorphous triphenylene compound described in chemical formula (8): 0.96 g (yield: 91.0%).

(8)

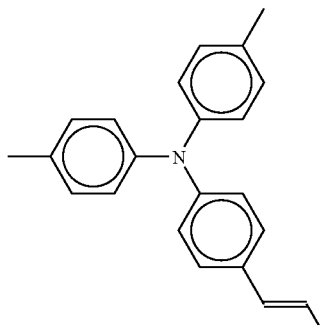
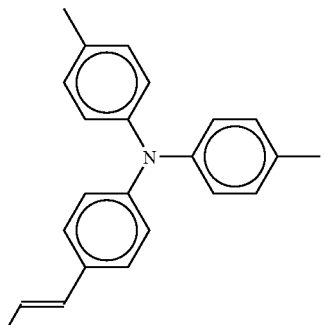
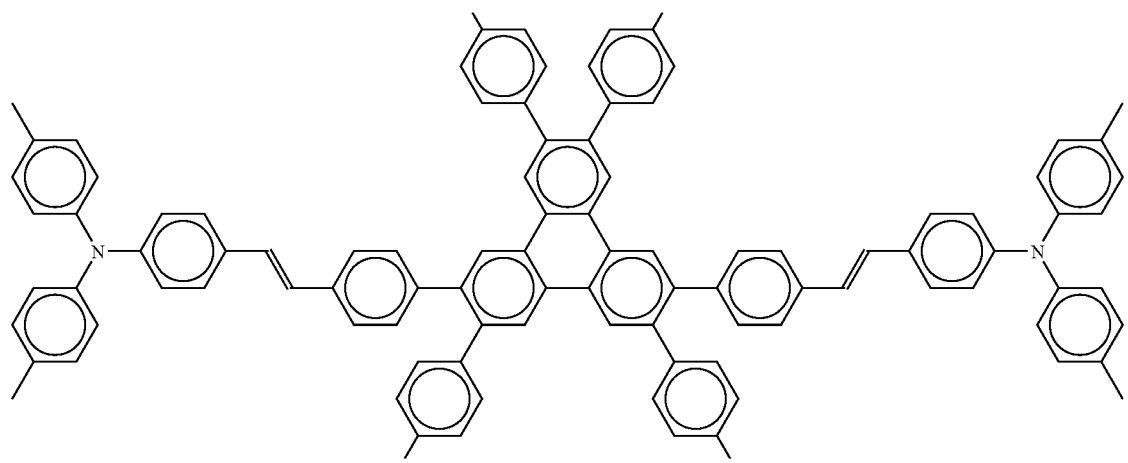
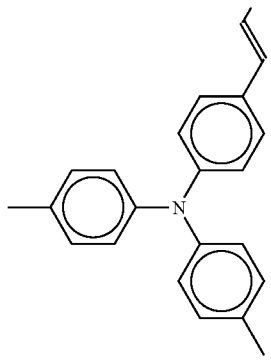
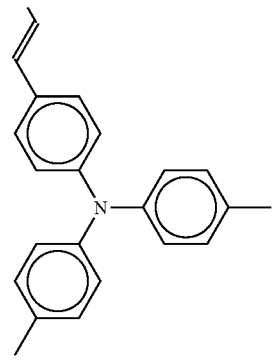

Elemental analysis of C150H126N6 is as follows.
|  | C (%) | H (%) | N (%) |
|---|---|---|---|
| Actual Measurement Value | 90.16 | 6.02 | 3.29 |
| Calculated value | 90.47 | 6.12 | 3.40 |
Infrared absorption spectrum (KBr pellet method) of this chemical compound (8) is shown in FIG. 1.
Example 4
Preparation of a Triphenylene Compound
A triphenylene compound may be prepared by reaction (9)
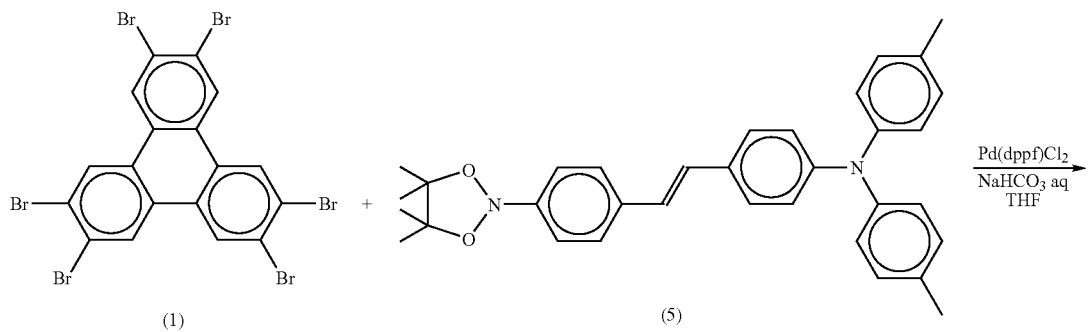
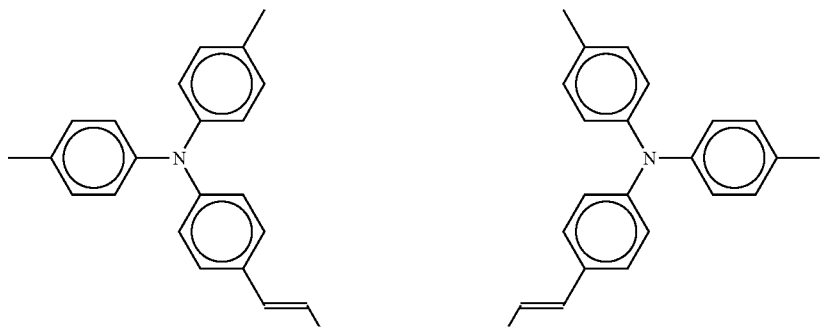
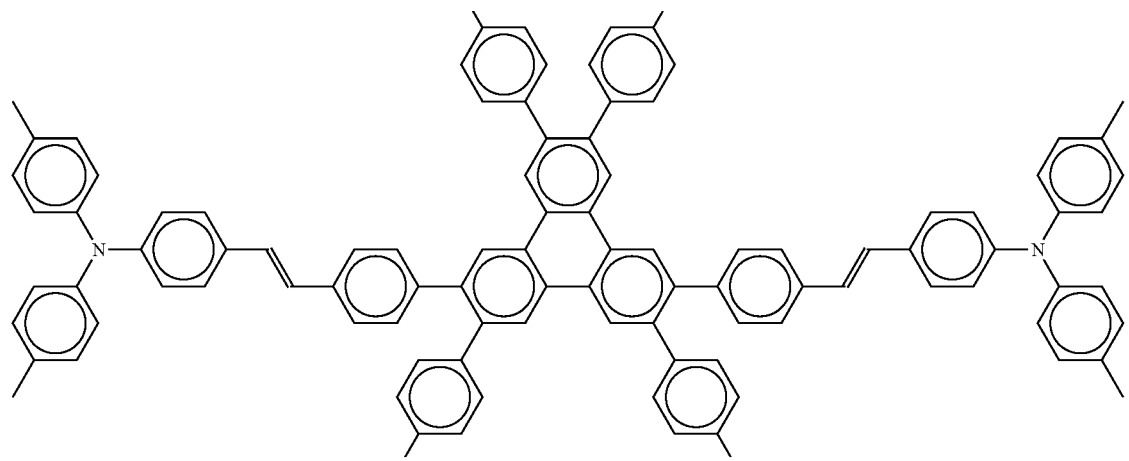

-continued

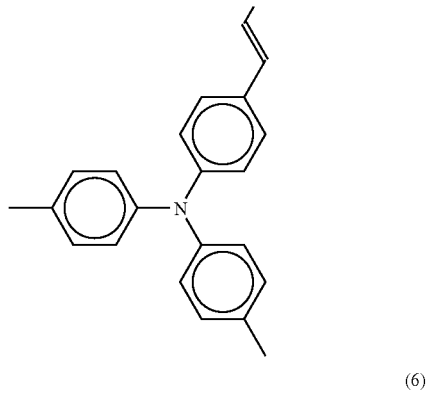

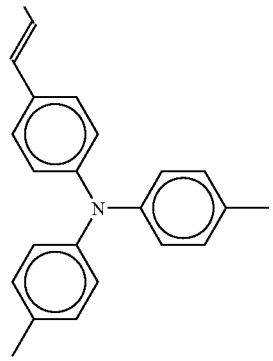

(6)

A mixture of hexabromo triphenylene (1): 0.2 g (0.0285 mmol), boron compound (5): 1.28 g (2.565 mmol), saturation NaHCO3: 10 ml 1,1'-bis(diphenylphosphino)ferrocene palladium (II) dichloride: 0.187 g (0.2565 mmol), and THF: 20 ml is agitated for 7 hours at 100° C. and cooled off to room temperature. Then, water is added and extracted with toluene and washed with water. A dark yellow oil product from the organic layer is vacuum condensed and filtered by silica column chromatography [Eluant: MDC/n-hexan (1/2) vol] to provide a yellow amorphous triphenylene compound: 0.63 (yield: 89.9%).

Example 5

2.5 parts by weight fluororenebisazo pigment described in (10) as a charge material, 495 parts by weight tetrahydrofuran, and 2.5 parts by weight polyester resin (Trademark "Vylon200", made by Toyobo Co., Ltd.) were pulverized and dispersed in a ball mill.

The dispersion liquid was coated by a doctor blade on an aluminium evaporation polyester film and a charge generating layer was formed, a thickness of which was 0.5 μm, by drying naturally.

Next, a photoconductor of charge transport layer was provided. Charge transport material: triphenylene (4) was dissolved in 1 part by weight of Polycarbonate resin [PANLITE K-1300 made by Teijin Limited.] and 8 parts by weight of tetrahydrofuran resin liquid. The liquid was coated on a charge generation layer by doctor-blade followed by desiccation at 80° C. for 2 min and 120° C. for 5 min.

Next, to investigate the transit time (tr) of lamination type photoconductor, the electrostatic copy paper test apparatus [Kawaguchi Denki-Seisakusho Co, Ltd] was prepared. Transit time indicates response. The photoconductor was corona charged with the electrostatic copy paper test apparatus to negative, and the exposure time was 33 ms. After 1 second, the exposure amount which can light attenuation −800V to −100V was defined and then Transit time (tr) was calculated as follows:

$tr$=[Time for achieved −150V]−exposure time 33 ms

The result was tr=8 ms.

Comparative Example

The procedure for preparation of the electrophotographic photoreceptor in Example 5 was repeated to prepare an

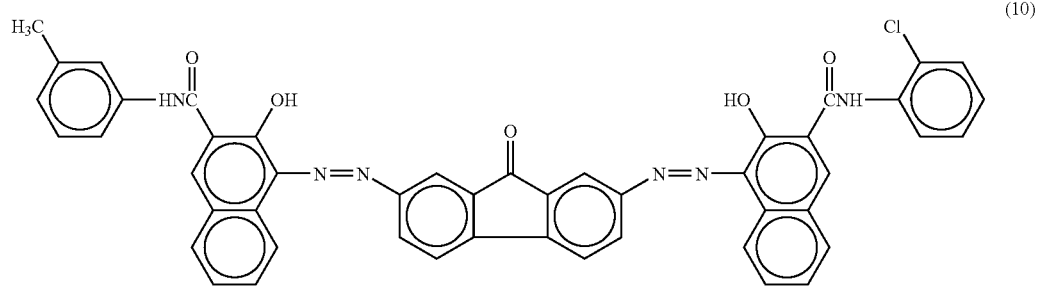

(10)

electrophotographic photoreceptor except for excluding triphenylene compound, and instead of triphenylene compound the amine compound (11) described below was used.

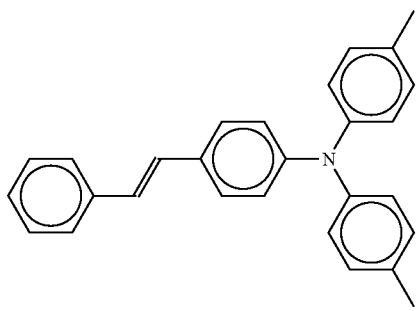

Transit time was measured as in Example 5 above. The result was tr=22 ms.

What is claimed as new and desired to be secured by Letters Patent of the United States is:

1. A triphenylene compound of formula 1:

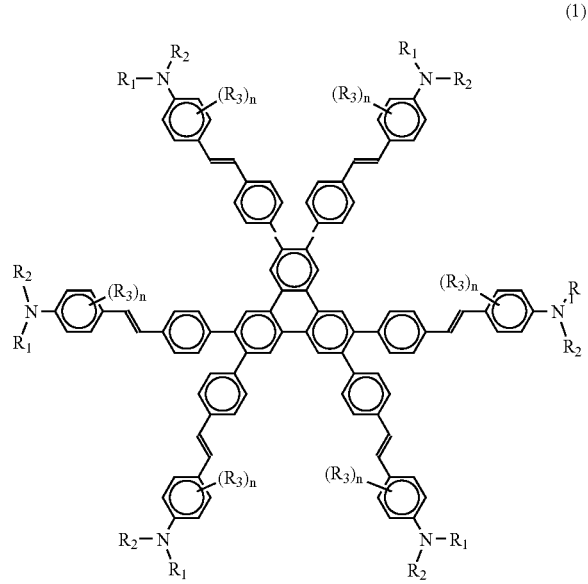

wherein R1 and R2 independently represent a substituted or unsubstituted alkyl group, or a substituted or unsubstituted aromatic hydrocarbon group and may be combined with each other to form a substituted or unsubstituted heterocyclic group including the nitrogen atom to which they are appended;

R3 independently represents a hydrogen atom, a substituted or unsubstituted alkyl group, a substituted or unsubstituted alkoxy group, a substituted or unsubstituted aromatic hydrocarbon group, or a halogen atom; and n independently represents an integer of from 1 to 4.

2. A method for manufacturing a triphenylene compound, comprising:

reacting 2,3,6,7,10,11-hexabromotriphenylene having the following formula (2) with at least one boron compound selected from boron compounds having the following formulae (3) and (4):

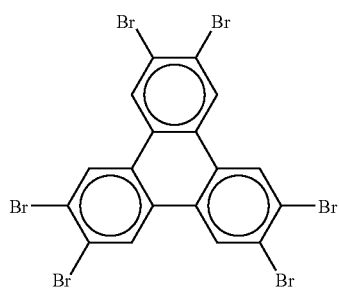

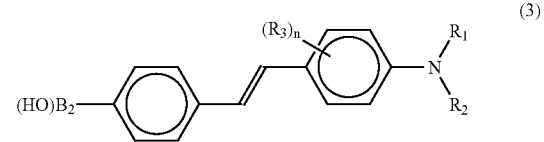

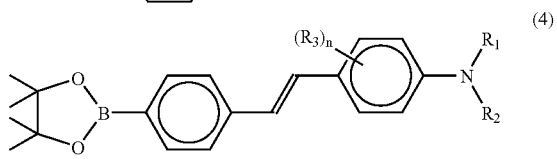

wherein R1 and R2 independently represent a substituted or unsubstituted alkyl group, or a substituted or unsubstituted aromatic hydrocarbon group and may be combined with each other to form a substituted or unsubstituted heterocyclic group including the nitrogen atom to which they are appended;

R3 independently represents a hydrogen atom, a substituted or unsubstituted alkyl group, a substituted or unsubstituted alkoxy group, a substituted or unsubstituted aromatic hydrocarbon group, or a halogen atom; and n independently represents an integer of from 1 to 4.

3. The method for manufacturing a triphenylene compound according to claim 2, comprising:

reacting 2,3,6,7,10,11-hexabromotriphenylene with at least one boron compound having formula (3).

4. The method for manufacturing a triphenylene compound according to claim 2, comprising:

reacting 2,3,6,7,10,11-hexabromotriphenylene with at least one boron compound having formula (4).

5. The method for manufacturing a triphenylene compound according to claim 2, comprising:

reacting 2,3,6,7,10,11-hexabromotriphenylene with at least one boron compound having formula (3) and at least one boron compound having formula (4).

* * * * *